(12) United States Patent
Sumikawa et al.

(10) Patent No.: US 7,659,428 B2
(45) Date of Patent: Feb. 9, 2010

(54) METHODS FOR PRODUCING ACYLPHENYLALANINE

(75) Inventors: Michito Sumikawa, Yokkaichi (JP); Takao Ohgane, Yokkaichi (JP)

(73) Assignee: Ajinomoto Co., Inc., Tokyo (JP)

( * ) Notice: Subject to any disclaimer, the term of this patent is extended or adjusted under 35 U.S.C. 154(b) by 196 days.

(21) Appl. No.: 11/319,177

(22) Filed: Dec. 28, 2005

(65) Prior Publication Data

US 2006/0155143 A1 Jul. 13, 2006

Related U.S. Application Data

(63) Continuation of application No. 10/418,102, filed on Apr. 18, 2003, now Pat. No. 7,030,268, which is a continuation of application No. PCT/JP01/09068, filed on Oct. 16, 2001.

(30) Foreign Application Priority Data

Oct. 18, 2000 (JP) .............................. 2000-317603

(51) Int. Cl.
*C07C 229/00* (2006.01)
(52) U.S. Cl. .................. 562/445; 562/443; 562/444
(58) Field of Classification Search .................. 562/450, 562/443, 444, 445
See application file for complete search history.

(56) References Cited

U.S. PATENT DOCUMENTS

| 6,844,008 B2 | 1/2005 | Yabuki et al. |
| 2003/0021843 A1 | 1/2003 | Makino et al. |
| 2003/0073729 A1 | 4/2003 | Kitahara et al. |
| 2003/0229249 A1 | 12/2003 | Sumikawa et al. |
| 2004/0014815 A1 | 1/2004 | Ninomiya et al. |
| 2004/0024219 A1 | 2/2004 | Sumikawa et al. |
| 2004/0030182 A1 | 2/2004 | Takahashi et al. |

FOREIGN PATENT DOCUMENTS

| EP | 0 093 551 A2 | 11/1983 |
| EP | 0 196 222 A2 | 10/1986 |
| EP | 0526171 | * 2/1993 |
| JP | 58-189121 | 11/1983 |
| JP | 59-190926 | 10/1984 |
| JP | 63-054321 | 3/1988 |
| JP | 5-70418 | 3/1993 |
| JP | 6-157440 | 6/1994 |
| JP | 6-256276 | 9/1994 |
| JP | 07-017899 | * 1/1995 |

OTHER PUBLICATIONS

XP-002333872, W.H. Kruizinga, et al., "Synthesis of Optically Pure α-Alkylated α-Amino Acids and a Single-Step Method for Enantiomeric Excess Determination", Journal of Organic Chemistry, vol. 53, No. 8, 1988, pp. 1826-1827.
XP-008049195, A. Kolbe, et al., "Diphenylessigsäure: Synthese, Papier-Und Dünnschicht-Chromatographische Sowie Massenspektroskopische Eigenschaften Von Aminosäurederivaten[1]", Journal Fuer Praktische Chemie, vol. 323, No. 2, 1981, pp. 311-318.
XP-008049199, J. You, et al., "Synthesis of New Chiral Macrocyclictetraoxo Polyamines Containing Pyridine Ring and Functional Arms", vol. 29, No. 14, 1999, pp. 2447-2455.

* cited by examiner

*Primary Examiner*—Taylor Victor Oh
(74) *Attorney, Agent, or Firm*—Oblon, Spivak, McClelland, Maier & Neustadt, L.L.P.

(57) ABSTRACT

There is provided a method for producing easily highly-purified acylphenylalanine that is useful as a raw material of pharmaceutical products and the like, which comprises the step of reacting an acid chloride with phenylalanine in a mixed solvent of an organic solvent and water, while keeping the solvent under the alkali condition by using potassium hydroxide.

11 Claims, No Drawings

METHODS FOR PRODUCING ACYLPHENYLALANINE

CONTINUING APPLICATION DATA

This application is a Continuation of application Ser. No. 10/418,102, filed on Apr. 18, 2003, now U.S. Pat. No. 7,030,268 now allowed, which is a Continuation of International Application No. PCT/JP01/09068, filed on Oct. 16, 2001.

TECHNICAL FIELD OF THE INVENTION

The present invention relates to a method for producing easily highly-purified acylphenylalanine that is useful as a raw material of pharmaceutical products and the like.

BACKGROUND ART

Among methods for producing an acylamino acid, the acylamino acid containing impurities as little as possible may be obtained by reacting a carboxylic acid corresponding to an acyl group with an amino acid ester in the presence of a condensing agent such as dicyclohexylcarbodiimide (DCC) and then hydrolyzing the ester. However, because the method requires preparation of an amino acid ester once and usage of an expensive condensing agent, it has a disadvantage in high production cost.

As regards another method for producing an acylamino acid, which uses an amino acid instead for an amino acid ester, it is known that the acylamino acid may be obtained by reacting a carboxylic acid with N-hydroxy succinimide in the presence of DCC and the like to form an activated ester, and then reacting the activated ester with an amino acid. However, because the method also requires usage of an expensive condensing agent and its yield is not high, it raises the production cost.

At present, as regards the method for producing an acylamino acid at low cost, Schotten-Baumann reaction is considered to be the most industrially-superior reaction, wherein an acid chloride and an amino acid are reacted in an aqueous solvent under the alkali condition. The reaction is used for the production of various acylamino acids.

Though Schotten-Baumann reaction tried to be applied to the production of acylphenylalanine, it was found that impurities were produced in the reaction and they were not easily removed.

DISCLOSURE OF THE INVENTION

Therefore, an object of the present invention is to provide a method for preventing the production of impurities when acylphenylalanine is produced by using industrially-superior Schotten-Baumann reaction.

The inventors have closely examined the impurities which are by-product formed through the production of acylphenylalanine by using Schotten-Baumann reaction and found that the impurities are acylphenylalanyl-phenylalanine (AcPP), wherein acylphenylalanine is further combined with phenylalanine.

For the purpose of preventing the production of AcPP, the inventors have vigorously studied and unexpectedly found that the purpose can be easily achieved by using potassium hydroxide as a neutralizing agent in the reaction. The present invention has been completed on the basis of this finding. The present invention includes the following each invention:

(1) A method for producing acylphenylalanine, which comprises the step of reacting an acid chloride with phenylalanine in a mixed solvent of an organic solvent and water, while keeping the solvent under the alkali condition by using potassium hydroxide.
(2) The method according to (1), wherein pH of the mixed solvent is not less than 12.5.
(3) The method according to (1), wherein pH of the mixed solvent is not less than 13.5.
(4) The method according to (1), wherein a mixed ratio of the organic solvent to water in the mixed solvent is 10:90 to 80:20 by volume.
(5) The method according to (1), wherein a mixed ratio of the organic solvent to water in the mixed solvent is 15:85 to 40:60 by volume.
(6) The method according to (1), wherein the acid chloride is a saturated or unsaturated acid chloride having 2 to 22 carbon atoms.
(7) The method according to (1), wherein the acid chloride is selected from a group consisting of caproic chloride, caprylic chloride, capric chloride, lauric chloride, myristic chloride, palmitic chloride, stearic chloride, oleic chloride, cyclohexylcarbonyl chloride, methylcyclohexylcarbonyl chloride, ethylcyclohexylcarbonyl chloride, propylcyclohexylcarbonyl chloride, isopropylcyclohexylcarbonyl chloride, benzoyl chloride, toluoyl chloride, salicyloyl chloride, cinnamoyl chloride, naphthoyl chloride and nicotinic chloride.
(8) The method according to (1), wherein the acid chloride is isopropylcyclohexylcarbonyl chloride.
(9) The method according to (1), wherein the organic solvent in the mixed solvent is selected from a group consisting of acetone, methylethylketone, dioxane, tetrahydrofuran, acetonitrile, methanol, ethanol and isopropyl alcohol.
(10) The method according to (9), wherein the organic solvent in the mixed solvent is acetone.
(11) A method for producing acylphenylalanine, which comprises the steps of adding an acid chloride dropwise to a solution containing phenylalanine and potassium hydroxide in a mixed solvent of an organic solvent and water, while keeping the pH of the solution under the alkali condition by using potassium hydroxide.
(12) The method according to (11), wherein pH is not less than 12.5.
(13) The method according to (ii), wherein a mixed ratio of the organic solvent to water in the mixed solvent is 10:90 to 80:20 by volume.

BEST MODE FOR CARRYING OUT THE INVENTION

An acid chloride used in the present invention is not particularly limited but usually a saturated or unsaturated acid chloride having 2 to 22 carbon atoms, and preferably 6 to 18 carbon atoms. Examples thereof include an acid chloride derived from a fatty acid such as caproic acid, caprylic acid, capric acid, lauric acid, myristic acid, palmitic acid, stearic acid and oleic acid; cyclohexylcarbonyl chloride, methylcyclohexylcarbonyl chloride, ethylcyclohexylcarbonyl chloride, propylcyclohexylcarbonyl chloride, isopropylcyclohexylcarbonyl chloride, benzoyl chloride, toluoyl chloride, salicyloyl chloride, cinnamoyl chloride, naphthoyl chloride and nicotinic chloride. They may contain a substituent(s).

Further, the acid chloride of the present invention also includes alkyloxycarbonyl chloride such as methoxycarbonyl chloride and t-butoxycarbonyl chloride, and aryloxycarbonyl chloride such as benzyloxycarbonyl chloride in addition to the alkylcarbonyl chloride and the arylcarbonyl chloride.

An aqueous solution of potassium hydroxide is used for adjusting pH in the reaction. If the pH of the reaction mixture is not less than 10, the reaction proceeds without any problems, however, the higher pH of the reaction mixture is preferable because it prevents the generation of AcPP. Preferable pH is not less than 12, more preferably not less than 12.5, further more preferably not less than 13 and further more particularly preferably not less than 13.5. However, as the reaction mixture is sometimes colored in case pH is more than 14, the pH needs to be carefully adjusted when coloring should be avoided. Though the pH may deviate from the above range in adjusting it, if temporary, it does not particularly cause problem as the temporary deviance does not have a negative impact. The value of pH is herein indicated by a reading of a pH meter with glass electrodes. The concentration of the aqueous potassium hydroxide solution is not particularly limited, but usually 2 to 50% by weight, preferably 5 to 25% by weight.

The organic solvents herein used are those which may be miscible with water. For example, they include acetone, methylethylketone, dioxane, tetrahydrofuran, acetonitrile, methanol, ethanol, propanol and isopropanol, and especially acetone is preferred.

The mixed ratio of an organic solvent to water depends on the acid chlorides used and therefore, can not be generally defined. However, it is usually 10:90 to 80:20 and preferably 15:85 to 40:60. The lower ratio of the organic solvent tends to prevent the production of by-product, AcPP. However, when an acyl group contains a large number of carbon atoms, which leads to an intended compound being high hydrophobicity, the ratio of the organic solvent needs to be heightened in order to prevent the compound from prepicitation and solidification during the reaction. The ratio herein indicates a volume ratio of an organic solvent to water and an aqueous solution of potassium hydroxide added at the start point of the reaction.

The temperature and the concentration of the reaction also can not be generally defined, because they depend on the acid chlorides used and the reaction solvents used. However, the reaction temperature is usually −5 to 25° C. and preferably 0 to 15° C. The reaction concentration is usually 1 to 20% and preferably 2 to 10%. Their appropriate conditions can be determined in view of their yields, operationality and productivity.

As for the reaction methods, the following method can be applied, for instance. First, phenylalanine is dissolved in water by using approximate equivalent molar amount of aqueous potassium hydroxide solution and an organic solvent is added thereto. Aqueous potassium hydroxide solution is further added to adjust pH. Then an acid chloride is added dropwise with stirring. The drop time is preferably from about 15 minutes to about 2 hours. The molar ratio of phenylalanine to an acid chloride such as trans-4-isopropylcyclohexylcarbonyl chloride used in the reaction is suitably 0.5:1 to 2:1, preferably 0.9:1 to 1.5:1. The concentration in the reaction of phenylalanine with the acid chloride such as trans-4-isopropylcyclohexylcarbonyl chloride is preferably 2wt % to 15wt % in terms of the concentration of phenylalanine, when each substance is within the above range. The acylphenylalanine produced can be crystallized by making the reaction mixture acidic with hydrochloric acid and the like, filtered out, and taken out by being washed with water.

EXAMPLES

The following Examples will further illustrate the present invention, which by no means limit the invention.

Example 1

17 ml of water and 10.5 ml of 10% potassium hydroxide aqueous solution were added to 4.2 g of phenylalanine to dissolve it. 50 ml of acetone was added thereto and cooled to about 10° C. 5.5 g of trans-4-isopropylcyclohexylcarbonyl chloride (purity: about 95%) was added dropwise to the reaction mixture. In the meanwhile, 10% potassium hydroxide aqueous solution was added to the reaction mixture, while keeping the pH of the mixture being 10.5 to 11.0. Then, the reaction mixture was analyzed by HPLC to calculate an area ratio of impurities [trans-4-isopropylcyclohexylcarbonyl phenylalanyl-phenylalanine (IPP)] to an intended compound (trans-4-isopropylcyclohexylcarbonyl phenylalanine). The result is shown in Table 1.

Examples 2 to 6

The following reactions of Examples 2 to 6 were conducted by using 10% potassium hydroxide aqueous solution and by the same procedure as that of Example 1, except that the concentration of the organic solvents and the pH in the reaction were changed as shown in Table 1. The reaction mixtures were analyzed by HPLC in a similar manner to that of Example 1. The results are shown in Table 1.

TABLE 1

| Example | Alkali | Organic solvent | pH | IPP |
|---|---|---|---|---|
| 1 | KOH | 65% acetone | 10.5 to 11 | 0.6 |
| 2 | KOH | 60% acetone | 12 to 13 | 0.5 |
| 3 | KOH | 50% acetone | 12 to 13 | 0.3 |
| 4 | KOH | 40% acetone | 12 to 13 | 0.13 |
| 5 | KOH | 30% acetone | 12 to 13 | 0.08 |
| 6 | KOH | 20% acetone | 12 to 13 | 0.05 |

Examples 7 to 9

44 ml of water and 16 ml of 10% potassium hydroxide aqueous solution were added to 4 g of phenylalanine to dissolve it. 15 ml of acetone was added thereto and cooled down to about 10° C. 5.3 g of trans-4-isopropylcyclohexylcarbonyl chloride was added dropwise to the reaction mixture. In the meanwhile, 10% potassium hydroxide aqueous solution was added to the reaction mixture, while keeping the pH of the mixture being the values shown in Table 2. Then, the reaction mixtures were analyzed by HPLC in a similar manner to that of Example 1. The results are shown in Table 2.

TABLE 2

| Example | Alkali | Organic solvent | pH | IPP |
|---|---|---|---|---|
| 7 | KOH | 20% acetone | 12 to 12.5 | 0.13 |
| 8 | KOH | 20% acetone | 13 to 13.2 | 0.07 |
| 9 | KOH | 20% acetone | 13.7 to 13.8 | ND |

Examples 10 to 12

The following reactions of Examples 10 to 12 were conducted by the same procedure as that of Examples 7 to 9, except that the concentration of the organic solvents were changed and pH was 13.6 to 13.9. The reaction mixtures were analyzed by HPLC in a similar manner to that of Example 1. The results are shown in Table 3.

TABLE 3

| Example | Alkali | Organic solvent | pH | IPP |
|---|---|---|---|---|
| 10 | KOH | 20% acetone | 13.6 to 13.9 | ND |
| 11 | KOH | 30% acetone | 13.6 to 13.9 | ND |
| 12 | KOH | 40% acetone | 13.6 to 13.9 | 0.1 |

Comparative Example 1

17 ml of water and 10.5 ml of 10% sodium hydroxide aqueous solution were added to 4.2 g of phenylalanine to dissolve it. 50 ml of acetone was added thereto and cooled down to about 10° C. 5.5 g of trans-4-isopropylcyclohexyl-carbonyl chloride (purity: about 95%) was added dropwise to the reaction mixture. In the meanwhile, 10% sodium hydroxide aqueous solution was added to the reaction mixture, while keeping the pH of the mixture being 10 to 10.5. Then, the reaction mixture was analyzed by HPLC to calculate an area ratio of impurities [trans-4-isopropylcyclohexylcarbonyl phenylalanyl-phenylalanine (IPP)] to an intended compound (trans-4-isopropylcyclohexylcarbonyl phenylalanine). The result is shown in Table 4.

Comparative Examples 2 to 5

The following reactions of Comparative Examples 2 to 5 were conducted by using 10% sodium hydroxide aqueous solution and by the same procedure as that of Comparative Example 1 except that the ratio of the organic solvents and the pH in the reaction were changed. The reaction mixtures were analyzed by HPLC in a similar manner to that of Comparative Example 1. The results are shown in Table 4.

TABLE 4

| Comparative Example | Alkali | Organic solvent | pH | IPP |
|---|---|---|---|---|
| 1 | NaOH | 65% acetone | 10 to 10.5 | 1.9 |
| 2 | NaOH | 65% dioxane | 10 to 10.5 | 1.6 |
| 3 | NaOH | 65% acetonitrile | 10 to 10.5 | 1.8 |
| 4 | NaOH | 65% acetone | 12 to 12.5 | 3.5 |
| 5 | NaOH | 75% acetone | 10 to 10.5 | 3.9 |

It is apparent from comparison between the results of each Example and those of each Comparative Example described in Tables 1 to 4 that the production of IPP, which are impurities, can be considerably prevented by using potassium hydroxide aqueous solution as an alkali used in the reaction. Further, it is apparent from Examples 1 to 6 wherein the potassium hydroxide aqueous solution is used as an alkali that the lower concentration of the organic solvent (acetone) can prevent the production of IPP more effectively. However, in the methods wherein the starting materials of Examples 1 to 6 are used, it was confirmed that less usage amount of an acetone solvent than that of Example 6, for example, less than 10%, solidified the reaction mixture and made the continuation of the reaction difficult.

According to the method of the present invention, it is possible to produce easily highly-purified acylphenylalanine by industrially-superior Schotten-Baumann reaction.

What is claimed is:

1. A method for producing purified trans-4-isopropylcyclohexylcarbonylphenylalanine, which comprises reacting a trans-4-isopropylcyclohexylcarbonyl chloride with phenylalanine in a mixed solvent of acetone and water, while keeping the pH of the mixed solvent at not less than 12.5 by using potassium hydroxide,
wherein the ratio of acetone to water in the mixed solvent is 10:90 to 80:20 by volume.

2. The method of claim 1, wherein pH of the mixed solvent is not less than 13.5.

3. The method of claim 1, wherein the ratio of acetone to water in the mixed solvent is 15:85 to 40:60 by volume.

4. The method of claim 1, wherein the pH is not less than 13.5 and the ratio of acetone to water in the mixed solvent is 15:85 to 40:60 by volume.

5. The method of claim 1, wherein the pH is not more than 14.

6. The method of claim 2, wherein the pH is not more than 14.

7. The method of claim 4, wherein the pH is not more than 14.

8. The method of claim 1, wherein the reaction temperature is −5 to 25° C.

9. The method of claim 1, wherein the reaction temperature is 0 to 15° C.

10. The method of claim 1, wherein the reaction concentration is 1 to 20%.

11. The method of claim 1, wherein the reaction concentration is 2 to 10%.

* * * * *